United States Patent [19]

Rosen et al.

[11] Patent Number: 5,501,671
[45] Date of Patent: Mar. 26, 1996

[54] VASCULAR BLOOD CONTAINMENT DEVICE

[75] Inventors: Jonathan J. Rosen, Alpharetta; Richard A. Hillstead, Duluth; Thomas D. Weldon, Gainesville; Charles E. Larsen, Cumming, all of Ga.; David O. Williams, Barrington, R.I.

[73] Assignee: Novoste Corporation, Norcross, Ga.

[21] Appl. No.: 146,555

[22] Filed: Nov. 2, 1993

[51] Int. Cl.⁶ .................................................. A61M 5/178
[52] U.S. Cl. ........................................... 604/168; 604/164
[58] Field of Search .................................. 604/168, 167, 604/118, 164

[56] References Cited

U.S. PATENT DOCUMENTS

| | | | |
|---|---|---|---|
| 3,734,095 | 5/1973 | Santomieri | 128/214.4 |
| 4,016,879 | 4/1977 | Mellor | 128/214.4 |
| 4,020,835 | 5/1977 | Nordstrom et al. | 128/214.4 |
| 4,108,175 | 8/1978 | Orton | 128/214.4 |
| 4,652,256 | 3/1987 | Vaillancourt | 604/52 |
| 4,655,750 | 4/1987 | Vaillancourt | 604/165 |
| 4,738,658 | 4/1988 | Magro et al. | 604/53 |
| 4,758,218 | 7/1988 | Kiefer et al. | 604/53 |
| 4,767,408 | 8/1988 | McFarlane | 604/168 |
| 4,838,269 | 6/1989 | Robinson et al. | 128/344 |
| 4,904,240 | 2/1990 | Hoover | 604/53 |
| 4,946,443 | 8/1990 | Hauser et al. | 604/165 |
| 5,059,186 | 10/1991 | Yamamoto et al. | 604/280 |
| 5,066,284 | 11/1991 | Mersch et al. | 604/168 |
| 5,098,406 | 3/1992 | Sawyer | 604/207 |
| 5,108,375 | 4/1992 | Harrison et al. | 604/167 |

OTHER PUBLICATIONS

Arrow-Fischell EVAN Vascular Access Needle, advertisement. SoS Bloodless Entry Needle, advertisement.

*Primary Examiner*—John G. Weiss
*Attorney, Agent, or Firm*—Cook, Egan, McFarron & Manzo, Ltd.

[57] ABSTRACT

A blood containment, visualization and tactile confirmation device is provided for use with a vascular entry needle. The device includes a visualization channel and/or a complaint outer wall portion which indicates whether a needle connected to the device has entered a selected blood vessel. The visualization channel is vented to the outside to allow displaced air to escape, but has a gas permeable member to prevent blood from escaping. The visualization channel may have one, two, or more stages, with a first stage chamber which indicates initial penetration of a selected blood vessel, and a second stage chamber which fills more slowly and indicates that the needle remains positioned within the blood vessel. A third stage chamber with entrapped air which compresses slightly due to the heartbeat may also be used. Preferably, a compliant outer wall portion pulses with changes in blood pressure, thereby providing a tactile indication that the needle tip is properly positioned. The device has a guideway with a barrier of elastomeric material which prevents blood from passing therethrough, but which allows passage of an elongated medical instrument such as catheterization apparatus.

29 Claims, 6 Drawing Sheets

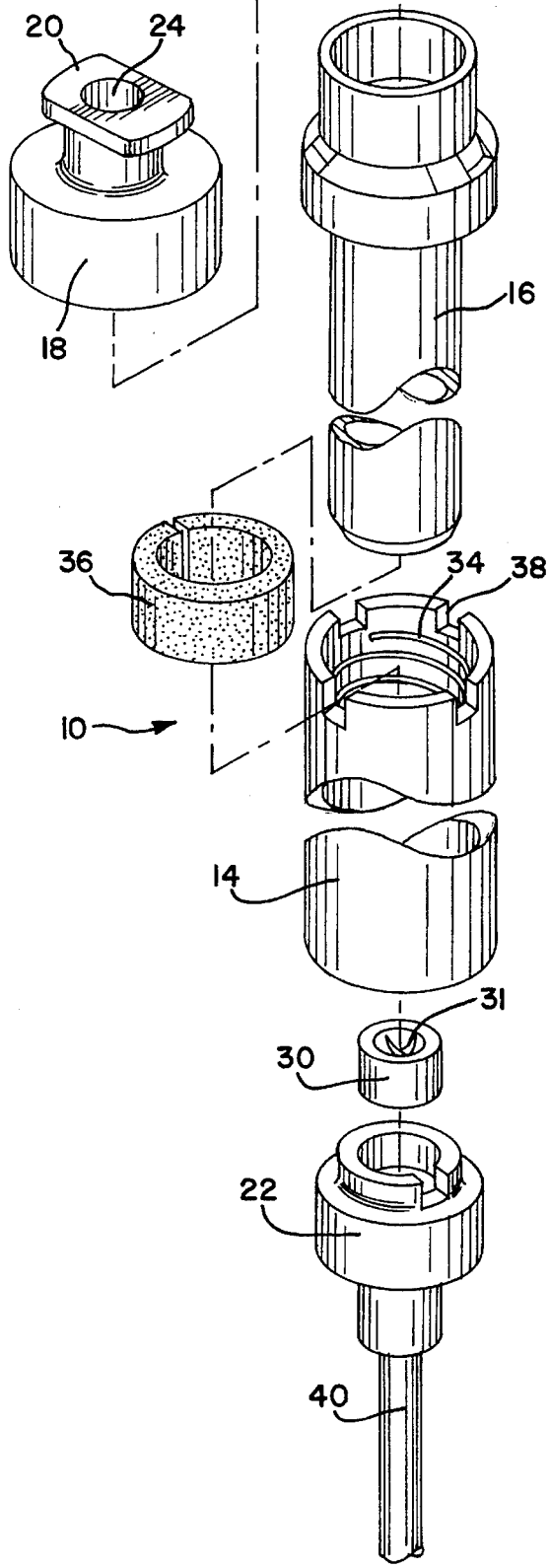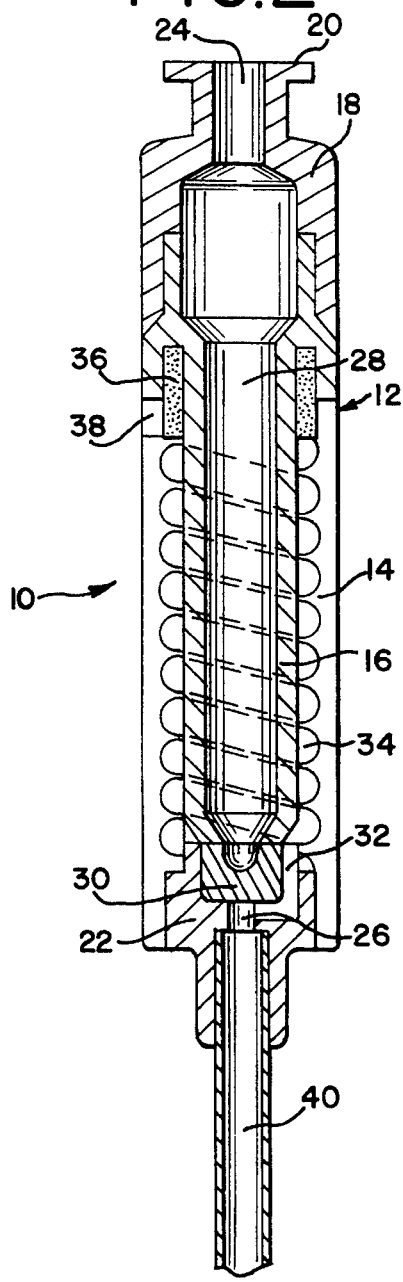

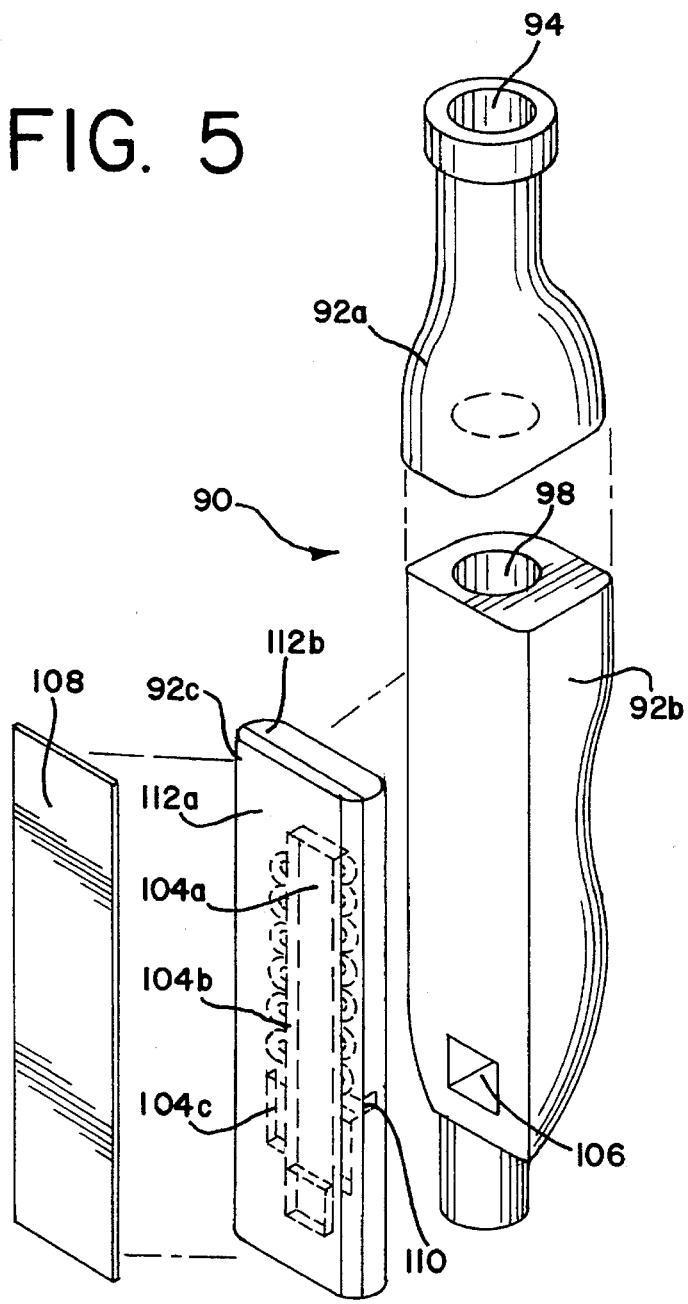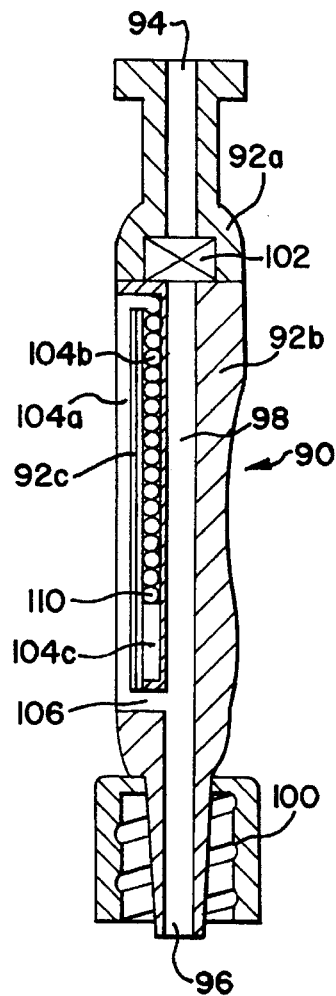

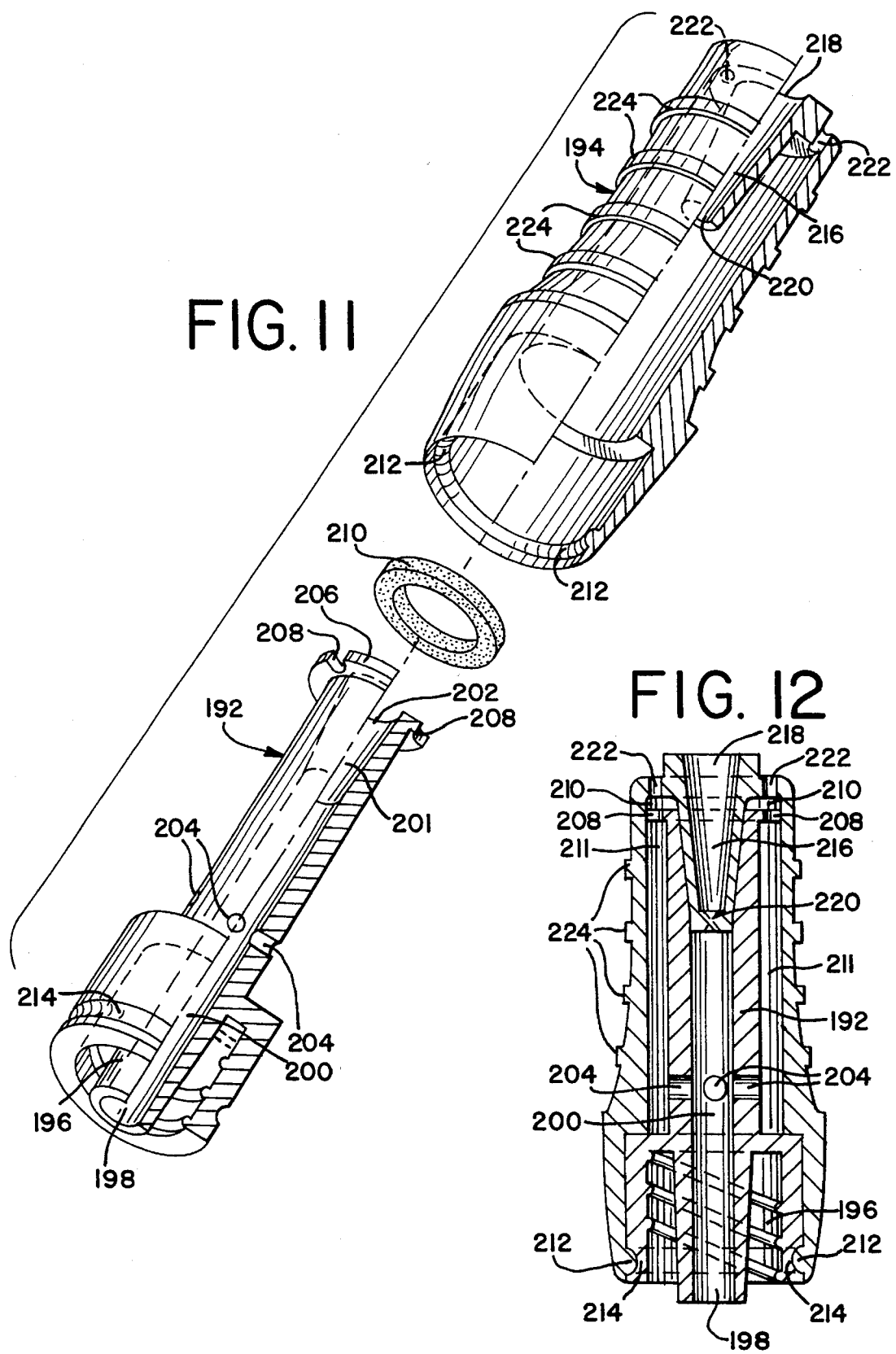

VASCULAR BLOOD CONTAINMENT DEVICE

BACKGROUND OF THE INVENTION

The present invention generally relates to vascular entry devices and, more particularly, to a blood containment device for use with a vascular entry needle which provides visual and/or tactile confirmation that the needle tip has entered into a blood vessel, particularly an artery, and allows for introduction of an elongated medical instrument, such as catheterization guide wire, or comparable apparatus, through the device.

It is a common medical procedure to insert a hollow needle into a patient's blood vessel for the purpose of either withdrawing blood or introducing a drug, guide wire, guide catheter, or the like into the blood vessel. One difficulty with such procedures, however, is determining when the tip of the needle is properly placed within the selected blood vessel. Another concern is that unless the blood is contained, vascular pressure, arterial pressure in particular, will force a leakage or spray of blood through the needle and escape through the other end of the needle. This can create a risk for the medical personnel of exposure to blood-borne viruses, such as hepatitis and HIV, which may be present in the patient's blood.

The problems with blood containment and confirming needle placement are particularly applicable during the procedure for introducing a guide wire, catheter, or the like, into a patient's artery for carrying out procedures in or around the patient's heart. Such catheterization involves first creating access to the selected artery using a vascular entry needle of sufficient bore, and then inserting a guide wire, guide catheter, or other catheter apparatus through the needle and into the selected artery. Often, the guide wire is first inserted and located in the proper position, and the catheter is then inserted over the guide wire. Self-guiding catheters may also be inserted without first using a guide wire. After the catheter apparatus is in position, the vascular entry needle can be removed by sliding it backwards over and off the proximal end of the guide wire apparatus.

In performing a catheterization procedure, as noted above, it is crucial that the vascular entry needle be properly positioned within the selected blood vessel. When an ordinary entry needle is used, entry of the needle tip into the blood vessel is indicated by the escape of blood at the proximal end of the needle. However, this has the attendant contamination problems mentioned above.

Another problem is that, during positioning, the needle can be accidentally pulled out of the blood vessel or pushed through the opposite side of the vessel wall, which defeats the catheterization procedure. Accordingly, it is important after the needle tip first enters the blood vessel to confirm that it remains properly positioned within the blood vessel.

Various blood containment devices exist in the prior art which are directed to solving the above problems. Two such devices are the AngioDynamics™ SOS Bloodless™ Entry Needle (U.S. Pat. No. 5,122,121) and the Arrow-Fischell EVAN™ Vascular Entry Needle. Both of these devices have a vascular entry needle attached to a transparent plastic containment member. The plastic containment member has a catheter guideway extending therethrough which allows insertion of catheterization apparatus through the device. The catheter guideway has a barrier within it which blocks blood from escaping, but allows passage of the catheterization apparatus.

Both devices also have features for indicating when the needle tip enters a blood vessel. The AngioDynamics™ SOS Bloodless™ Entry Needle has a length of transparent, flexible plastic tubing which branches off from the plastic containment member and leads to a small, collapsed, transparent plastic blood bag. When the needle tip is inserted into an artery, blood travels through the needle, into the guideway of the plastic containment member, out through the plastic tubing, and into the small blood bag. The soft plastic tubing of this device purportedly permits palpitation and visualization of the arterial pulse. However, the attached tube and blood bag can be cumbersome, particularly once the blood bag is filled. Also, once the blood bag is filled, the visual confirmation of needle tip placement stops.

The Arrow-Fischell EVAN™ Vascular Entry Needle provides for visualization of blood in a different way. The lower portion of the catheter guideway is narrow (about equal to the needle bore) for approximately two inches. It then opens into an air chamber near the upper portion of the device. When the tip of the vascular entry needle enters an artery, blood travels under pressure through the needle and partially fills the narrow lower portion of the guideway. It does this by slightly compressing the trapped air in the air chamber at the upper portion of the device. The thin column of blood then pulses back and forth in the guideway in response to the patient's heartbeat. This provides a visual indication that the needle tip is in a blood vessel. However, it can sometimes be difficult for a user of the device to see movement of the blood column, and there is no provision for tactile detection of the pulsating blood pressure.

Accordingly, it is a principal object of the present invention to provide an improved device which allows for convenient visual and/or tactile confirmation of when an associated vascular entry needle enters a selected blood vessel, but which contains the blood to prevent its escape, with the attendant contamination risks.

SUMMARY OF THE INVENTION

These objects, as well as others that will become apparent upon reference to the accompanying drawings and following detailed description, are provided by a blood containment device for use with a vascular entry needle, which device includes a main body having openings at opposite ends with a guideway extending therebetween. One opening is adapted to connect to the proximal end of a vascular entry needle, and the other opening provides access for an elongated medical instrument, such as a guide wire or catheter apparatus, to be inserted. A barrier is disposed in the guideway and restricts passage of blood through the guideway, but allows passage of the elongated medical instrument. The opening also allows for acceptance of a tapered syringe fitting to flush the device.

For observation of needle entry into the desired vessel, a blood visualization channel is provided within the housing in fluid communication with the guideway. The visualization channel has a vent to the outside environment with a gas permeable member interposed between the visualization channel and the outside environment. The gas permeable member allows passage of air, but prevents passage of blood. Upon insertion of the needle into a blood vessel, blood flows through the needle and into the visualization channel, thus indicating that the blood vessel has been entered.

Also, it is contemplated that the visualization channel may include at least two stages, a first stage chamber which fills quickly upon entry of the needle into a blood vessel, and a second stage chamber which fills more slowly with each pulse of the individual's heartbeat, thereby indicating that the needle tip remains positioned within the blood vessel. Further, a third stage chamber may be used which allows blood in the visualization channel to pulsate indefinitely even after the visualization channel is substantially filled. This provides ongoing visualization of the pulsating blood to confirm proper needle placement.

In the preferred embodiment of the invention, the housing of the device includes a wall with a compliant tactile membrane which is accessible from the exterior of the device. Blood pressure causes the membrane to bulge or pulse, which can be detected both visually and by tactile feedback by a user holding the device, thereby indicating that the vascular needle tip has entered a blood vessel. With proper needle placement in an artery, the membrane of the device will continue to pulsate with the patient's heartbeat, thus providing confirmation of proper arterial needle placement.

BRIEF DESCRIPTION OF THE DRAWINGS

FIG. 1 is a perspective exploded view of one embodiment of the invention;

FIG. 2 is a cross-sectional view of the embodiment shown in FIG. 1;

FIG. 5 is a perspective exploded view of another embodiment of the invention;

FIG. 6 is a cross-sectional view of the embodiment shown in FIG. 5;

FIG. 11 is a perspective exploded view, with a cut away section, of another embodiment of the invention; and FIG. 12 is a cross-sectional view of the embodiment shown in FIG. 11.

DETAILED DESCRIPTION OF THE INVENTION

Figure 3:
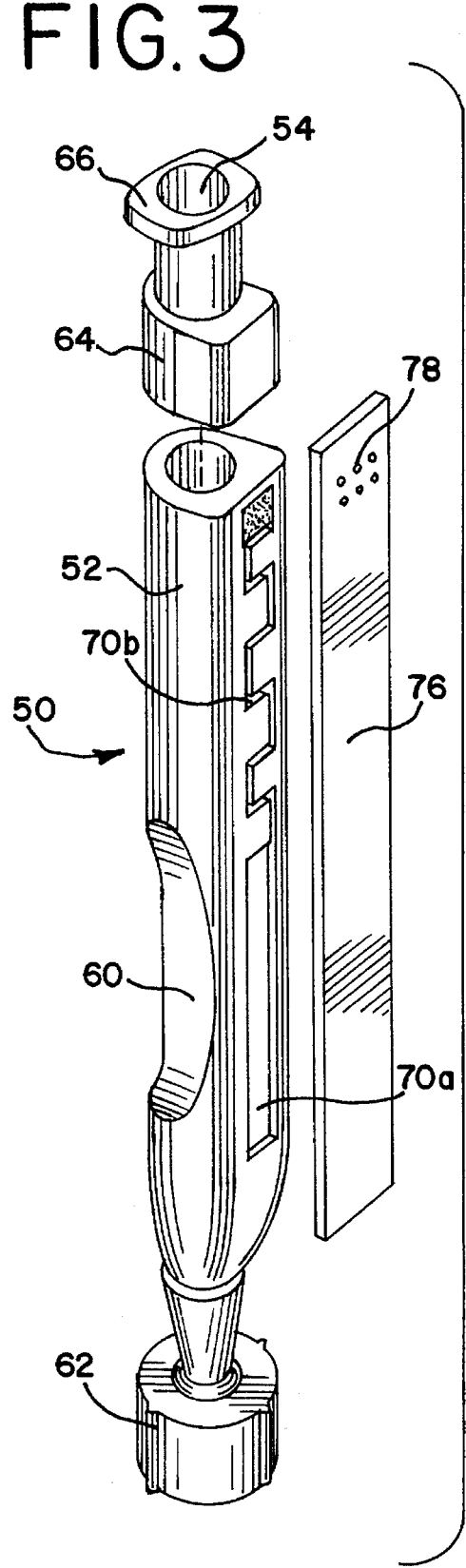
FIG. 3 is a perspective exploded view of another embodiment of the invention.

Referring first in general to the embodiment of the present invention depicted in FIGS. 1 and 2, various aspects of the present invention are embodied in a blood containment and visualization device 10 having a main body 12 with two openings: a distal opening 26 adapted to connect to a vascular entry needle, and a proximal opening 24 adapted to receive an elongated medical instrument such as a catheter or guide wire (not shown) of typical construction. A guideway 28 extends through the device between the two openings and has a barrier 30 interposed within it which prevents the passage of blood therealong, but allows the passage of an elongated medical instrument.

In accordance with the present invention generally, a blood visualization channel 34, which is visible to the user, is defined in the main body 12 of the device which communicates between the distal opening 26 and an air vent 38 to the outside. A gas permeable member 36 is disposed in the visualization channel and permits air, but not blood, to escape through the vent 38.

When used, entry into a blood vessel of a needle attached to the device is immediately apparent by blood entering into the visualization channel 34. Blood can travel through the visualization channel because air in the channel is allowed to escape through the vent 38 by the gas permeable member 36. The barrier 30 in the guideway 28 prevents blood from flowing therethrough and spurting out from the proximal opening 24.

In accordance with a further aspect of the present invention, described in detail below, the blood visualization channel may include two or more stages: a first stage chamber into which blood immediately flows when a blood vessel is first entered, and a second stage chamber through which blood flows more slowly to confirm that the needle remains in the vessel. A third stage chamber, described below in connection with FIGS. 5 and 6, may also be included which entraps a small volume of air within it after blood has reached the gas permeable member. This allows the blood to pulsate slightly by compressing the air and provides a further ongoing visual indication that the needle tip remains in the selected blood vessel.

In yet another aspect of the invention, described in connection with the embodiments of FIGS. 9–12, the exterior housing of the device may be comprised in whole or in part of a compliant tactile membrane. This membrane bulges due to blood pressure when the vascular entry needle tip enters a blood vessel. It then pulsates due to the pulsating blood pressure of the patient, and the user can thereby make tactile confirmation that the vascular needle tip is properly positioned within a selected blood vessel.

Turning now more specifically to the embodiment of FIGS. 1 and 2, the main body 12 is a generally cylindrical overall shape. The main body 12 is itself comprised of a number of components: an outer tubular member 14, an inner tubular member 16, a top cap member 18 with a female luer lock fitting 20, and a bottom fitting 22, designed to accept the proximal end of a vascular entry needle.

The assembled device includes at one end the proximal opening 24, at the other end the distal opening 26, and the guideway 28 extending therebetween, as best seen in FIG. 2. The components of the main body 12 are preferably constructed, as by injection molding, of rigid transparent plastic material to allow for visualization of blood through the device.

The barrier 30 is disposed in a recess of the bottom fitting 22 and held sealingly in place by axial pressure from the tip of the inner tubular member 16, as best seen in FIG. 2. Barrier 30 is preferably an elastomeric material, such as silicone rubber or latex, and has an aperture or slit 31 extending therethrough, as best seen in FIG. 1, to facilitate passage of an elongated medical instrument. Slit 31 can have any suitable configuration, such as being "X"-shaped, tricuspid, or single slit. Slit 31 is normally closed to prevent blood from traveling past barrier 30 and up through guideway 28. When an elongated medical instrument is inserted, slit 31 facilitates penetration of the instrument through the barrier 30 and also helps seal around the instrument to prevent blood from escaping past the barrier 30.

As best seen in FIG. 2, an L-shaped passage 32 leads from the distal opening 26 to the visualization channel 34. The visualization channel 34 is formed by helical grooves formed in the inner surface of outer tubular member 14, or the outer surface of 16. Inner tubular member 16 is sized to fit snugly within outer tubular member 14 and tightly contact the inner surface thereof, so that it confines blood flow within the helical grooves.

A gas permeable member 36 is disposed between outer tubular member 14 and inner tubular member 16 near the top of the helical grooves forming the visualization channel 34. Gas permeable member 36 is preferably a ring-shaped element of well known hydrophobic filter material, although a ceramic filter or any other material or structure which allows air to escape without allowing blood through will work. Vent notches 38 are located at spaced locations around the top of outer tubular member 14 to allow air to pass from the upper portion of the visualization channel 34 through gas permeable member 36 and out to the outside environment.

In operation, when the tip (not shown) of vascular entry needle 40 punctures a blood vessel, blood passes through the needle shaft and up to the distal opening 26. The blood is blocked by barrier 30 but travels through passage 32 to the helical passageway of visualization channel 34. Since the outer tubular member 14 is transparent, the blood is immediately visible in the lower portion of the visualization channel, indicating that the needle tip is within the selected blood vessel. As the user further positions the needle within the blood vessel or performs other steps, blood continues to pulse up through the upper portion of visualization channel 34, thus confirming that the needle tip remains within the selected blood vessel.

Air which is displaced as blood passes through visualization channel 34 escapes through gas permeable member 36 and out through vent notches 38. However, once blood reaches the top of visualization channel 34, it is blocked by gas permeable member 36, thus containing the blood within the device 10 and thereby reducing the risk of contamination.

The dimensions of the visualization channel are sufficiently narrow and its length sufficiently large that blood does not immediately fill the entire channel, but fills it gradually as the needle remains in the vessel. The sizes of the various passageways are preferably selected so that blood will pulse through the visualization channel 34 for up to 10 seconds or more. This allows sufficient time for the user to introduce the vascular entry needle into a selected blood vessel and verify that it remains properly positioned. The time for blood to fill the visualization channel may also be controlled by selecting a gas permeable member of the desired resistance to displaced air flow therethrough.

Once the vascular entry needle 40 is properly positioned, as verified by the present invention, an elongated medical instrument, such as a catheter or guide wire (not shown), can be inserted into proximal opening 24. The instrument is then maneuvered along guideway 28, through barrier 30, through the vascular entry needle 40, and along the selected blood vessel until located in the desired position. After being properly positioned, the elongated medical instrument can be attached in place to the male luer lock fitting 20 of the device. Alternatively, as is commonly done in a catheterization procedure, the entire containment and visualization device 10, along with the vascular entry needle 40, can be removed from the patient and slid back over and off of the catheterization apparatus, leaving the catheter or guide wire in place.

Figure 4:
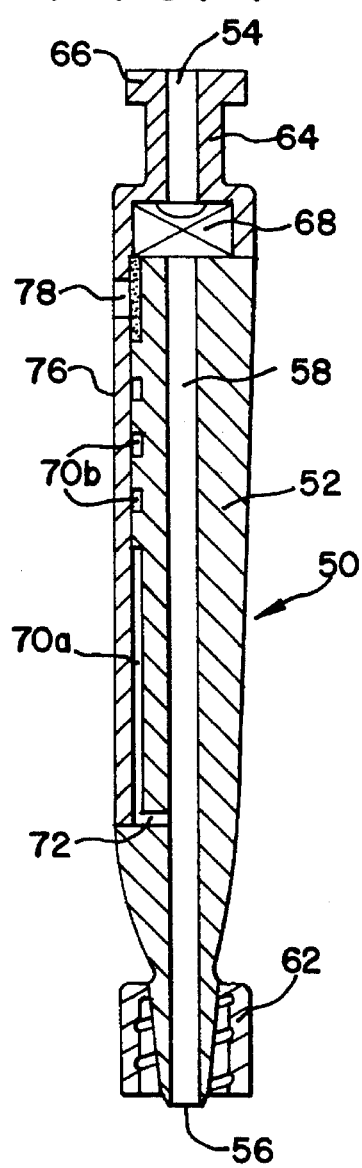
FIG. 4 is a cross-sectional view of the embodiment shown in FIG. 3.

Another embodiment of the invention is shown in FIGS. 3 and 4 as device 50. As best seen in FIG. 4, the main body 52 has a proximal opening 54 and a distal opening 56 connected via a guideway 58. A gripping depression 60 is formed along an exterior side of the main body 52 to facilitate gripping and handling of the device. Near the distal end of the device 50, is located a threaded male luer lock fitting 62 for attaching a standard vascular entry needle (not shown).

At the proximal end of the device 50 is a top cap portion 64 having a female luer lock fitting 66. The top cap portion 64 includes a recess within which the barrier member 68 is disposed, as seen in FIG. 4. As in the previously described embodiment, the barrier 68 is preferably made of an elastomeric material, such as silicone rubber or latex, having a slit therethrough to facilitate penetration by an elongated medical instrument. In FIG. 4, the presence of a slit is indicated schematically by the two crossed lines on the barrier 68.

A visualization channel 70a,b is formed along an exterior surface of the main body 52, as best seen in FIG. 3, and communicates with the guideway 58 via a passageway 72, as best seen in FIG. 4. The visualization channel 70a,b includes a first stage chamber 70a and a second stage chamber 70b. As best seen in FIG. 3, the first stage chamber 70a is a straight rectangular shaped channel running lengthwise along part of the main body 52. The first stage chamber is very shallow, but wide, so that it fills quickly and the blood can be seen vividly. The second stage chamber 70b is a narrower channel formed into a serpentine or square wave-like pattern. It is of sufficient volume and length so that blood takes up to 30 seconds to travel entirely through the second stage chamber 70b, thus allowing time for one using the device to position the needle and confirm that it remains properly positioned within the vessel.

At the uppermost (proximal) part of the second stage chamber 70b is located a gas permeable member 74, such as a hydrophobic filter element, well known in the art, which is permeable to gas but impermeable to liquid. A transparent cover plate 76 is sealed on the main body 52 over the visualization channel 70a,b to contain blood within the channel. Air vents 78 are located over the gas permeable member 74 to allow air displaced by blood traveling through the visualization channel to escape to the outside environment.

When a vascular entry needle attached to the embodiment of FIGS. 3 and 4 is introduced into a blood vessel, blood travels under pressure through the needle and into the distal opening 56. It then passes part way up the guideway 58, through the passageway 72, and into the visualization channel 70a,b. Blood quickly fills the first stage chamber 70a, thereby providing an immediate indication that the needle tip has entered a selected blood vessel. The second stage chamber 70b fills more slowly, taking up to 30 seconds or more, to confirm that the needle remains correctly positioned within the blood vessel.

As blood travels through the visualization channel 70a,b, displaced air passes through the gas permeable member 76 and escapes out air vents 78. Once blood reaches the gas permeable member 76, however, it is blocked from escaping to the outside environment; thus, substantially reducing the risk to medical personnel of infection by blood-borne diseases.

The procedure for inserting and positioning an elongated medical instrument, such as catheterization apparatus, through the device 50 is the same as described above in connection with the embodiment of FIGS. 1 and 2.

Another embodiment of the invention is shown in FIGS. 5 and 6. As best seen in FIG. 5, the device 90 has a main body 92a,b,c comprised of a top cap member 92a, a lower member 92*b*, and a side member 92*c*. The components are preferably made of rigid transparent plastic to allow for visualization of blood within the device. The main body 92*a,b,c* is contoured into a somewhat hourglass-like shape to facilitate gripping. As best seen in FIG. 6, there is a proximal opening 94 and a distal opening 96 connected via a guideway 98. A threaded male luer fitting 100, shown in FIG. 6, is located near the distal end of the lower body member 92*b*, which allows for connection of the device 90 to a standard vascular entry needle (not shown).

A normally closed barrier 102, shown in FIG. 6, is disposed in a recess of the top cap member 92*a* to prevent passage of blood through the guideway 98, but to allow passage of an elongated medical instrument (not shown). As noted above in connection with the previously described embodiments, barrier 102 is preferably made of an elastomeric material such as silicon rubber or latex and has a slit (indicated schematically by crossed lines) to facilitate penetration by the elongated medical instrument.

As best seen in FIG. 5, a visualization channel 104*a,b,c* is formed in the side member 92*c* and communicates with the guideway 98 via a passageway 106. The visualization channel includes three chambers: a first stage chamber 104*a*, a second stage chamber 104*b*, and a third stage chamber 104*c*.

The first stage chamber 104*a* is a shallow, wide channel running lengthwise along the outer surface of the side member 92*c*. A thin transparent cover plate 108 is disposed on the exterior of the side member 92*c* to contain blood within the first stage chamber 104*a* during use.

The first stage chamber connects near its uppermost (proximal) end to the uppermost (proximal) portion of the second stage chamber 104*b*. The second stage chamber 104*b* is comprised of a serpentine or zig-zag passageway running behind, but slightly wider than, the first stage chamber 104*a*, as best seen in FIG. 5. The second stage chamber is sufficiently long so as to take up to 30 seconds or more to fill with blood. At the lowermost (distal) end of the second stage chamber 104*b* is located an air vent 110 with a gas permeable member disposed therein which permits air from the first stage chamber 104*a* and second stage chamber 104*b* to escape to the outside environment.

The third stage chamber 104*c* communicates with the terminal end of the second stage chamber 104*b* and is also located behind the first stage chamber 104*a*. The third stage chamber 104*c* is wide enough so that its sides extend out past the first stage chamber 104*a*, as best seen in FIG. 5.

In order to construct the side member 92*c* having the visualization channel 104*a,b,c* as described, two halves 112*a,b* are used. The inner half 112*b* has the serpentine pattern of second stage chamber 104*b* and the third stage chamber 104*c* formed on the surface thereof. The outer half 112*a* has the first stage flash chamber 104*a* formed on its outwardly facing surface. When the two halves are bonded together, the back side of outer half 112*a* forms a cover to contain blood in the channels on the inner half 112*b*. The transparent cover 108 contains blood within the channel of outer half 112*a*.

When the device 90 is used, blood travels from guideway 98 through passage 106 and into the first stage chamber 104*a*, which fills almost immediately to visually indicate initial entry of the needle tip into a blood vessel. The blood then continues to travel into the second stage chamber 104*b* where it moves more slowly through the serpentine channel. The pulsatile flow in the second chamber indicates needle insertion into an arterial vessel.

Once blood reaches the gas permeable member disposed in the air vent 110, it is blocked so that no blood or air can escape. At this point, blood pressure slightly compresses air in the third stage chamber 104*c*, and blood will partially fill the chamber due both to blood pressure and capillary action. The third stage chamber 104*c* is sufficiently shallow so that the entrapped air will not be displaced by the blood up into the second stage chamber 104*b*. The blood partially filling the third stage chamber 104*c* will visibly pulsate with the changes in blood pressure due to the heartbeat. This provides confirmation for an indefinite length of time that the entry needle tip remains positioned within the selected blood vessel. Also, although the embodiment of FIGS. 5 and 6 is the only one showing the use of a third stage air chamber, it will be recognized that such a third stage chamber could be incorporated into the other embodiments as well.

After the needle is properly positioned, an elongated medical instrument can then be inserted through the device 90 as previously described.

Figure 7:
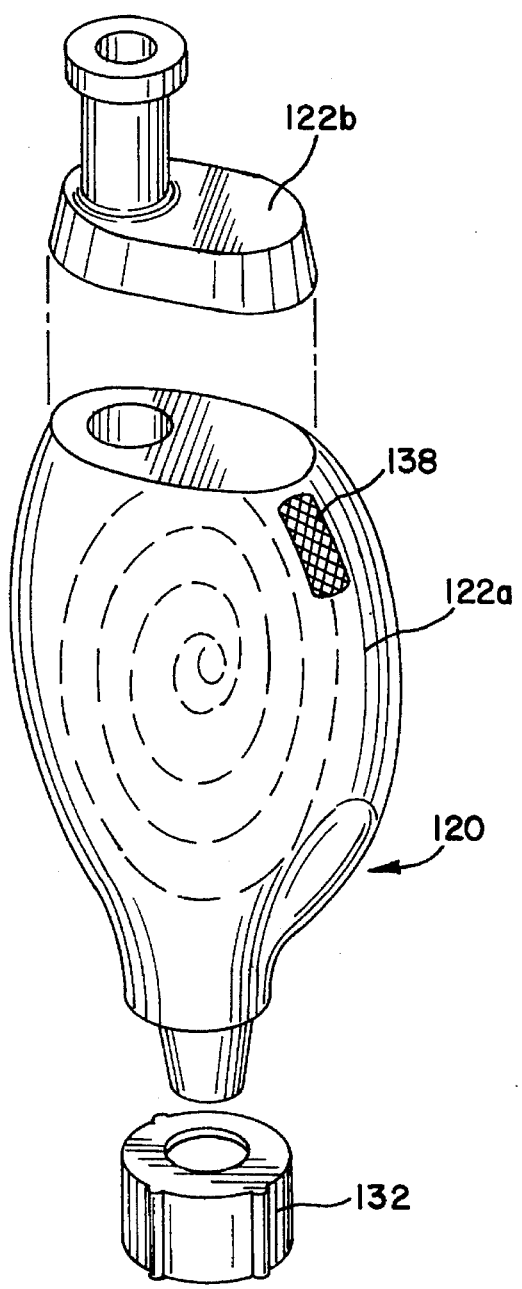
FIG. 7 is a perspective exploded view of another embodiment of the invention.
Figure 8:
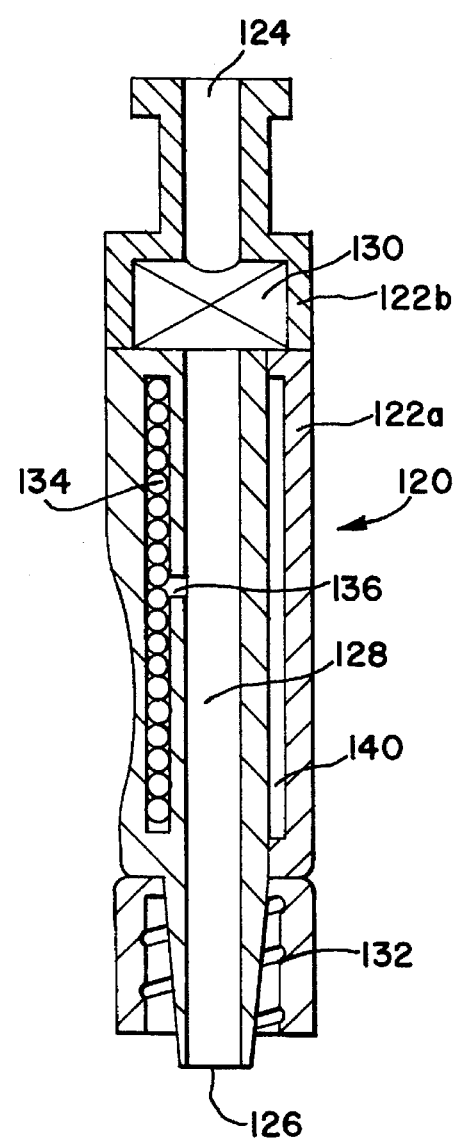
FIG. 8 is a cross-sectional view of the embodiment shown in FIG. 7.

A fourth embodiment of the invention is shown as device 120 in FIGS. 7 and 8. A main body 122*a,b* has a lower body member 122*a* and a top cap member 122*b*. The lower body member 122*a* is made of a rigid transparent plastic and has a somewhat flattened teardrop-like shape with contours to facilitate gripping, as best seen in FIG. 7. The top cap member 122*b* has a female luer lock fitting and bonds to the lower body member 122*a*.

As best seen in FIG. 8, a proximal opening 124 is connected to a distal opening 126 via a guideway 128. As in the previously described embodiments, a barrier 130 is interposed in guideway 128 to prevent passage of blood but allow passage of an elongated medical instrument. The barrier 130 is disposed in a recess of the top cap member 122*b*, and has a slit (indicated schematically by crossed lines and as described previously) to facilitate penetration by an elongated medical instrument (not shown).

A threaded male luer lock fitting 132 is located near the distal end of the main body 122*a* and allows connection to a standard vascular entry needle (not shown).

The device 120 has a spiral shaped visualization channel 134, as indicated by the dashed spiral line in FIG. 7, with the axis of the spiral running perpendicular to the axis of the guideway 128. The guideway 128 communicates with the center part (beginning) of the spiral shaped visualization channel 134 via a passage 136, as best seen in FIG. 8. As shown in FIG. 7, at the outermost or terminal end of the spiral shaped visualization channel 134 is located an air vent 138 having a gas permeable member disposed therein. The spiral shaped channel may be formed by molding the main body 122*a* of several different pieces, at least one, and preferably two, of which has a spiral shaped passageway formed in the surface, so that when the pieces are sealed together in facing relationship they define the spiral shaped channel 134 therebetween.

In operation, blood travels part way up through guideway 128, through passage 136, and into the spiral shaped visualization channel 134. The blood then pulses through the spiral passageway of the visualization channel 134, providing an indication of proper needle placement, until the blood reaches the gas permeable member at vent 138 where it is blocked from escaping. Also, if desired, a multiple stage visualization channel could be used with the embodiment of FIGS. 7 and 8. For example, a passage could be formed from the guideway 128 to another stage visualization chamber 140 illustrated in FIG. 8 on the side opposite the spiral shaped visualization channel 134. This other chamber could be used as a first stage chamber or a third stage air chamber, as described above in connection with the other embodiments.

Once the vascular entry needle has been properly positioned in the selected blood vessel, an elongated medical instrument can be introduced as previously described.

Figure 9:
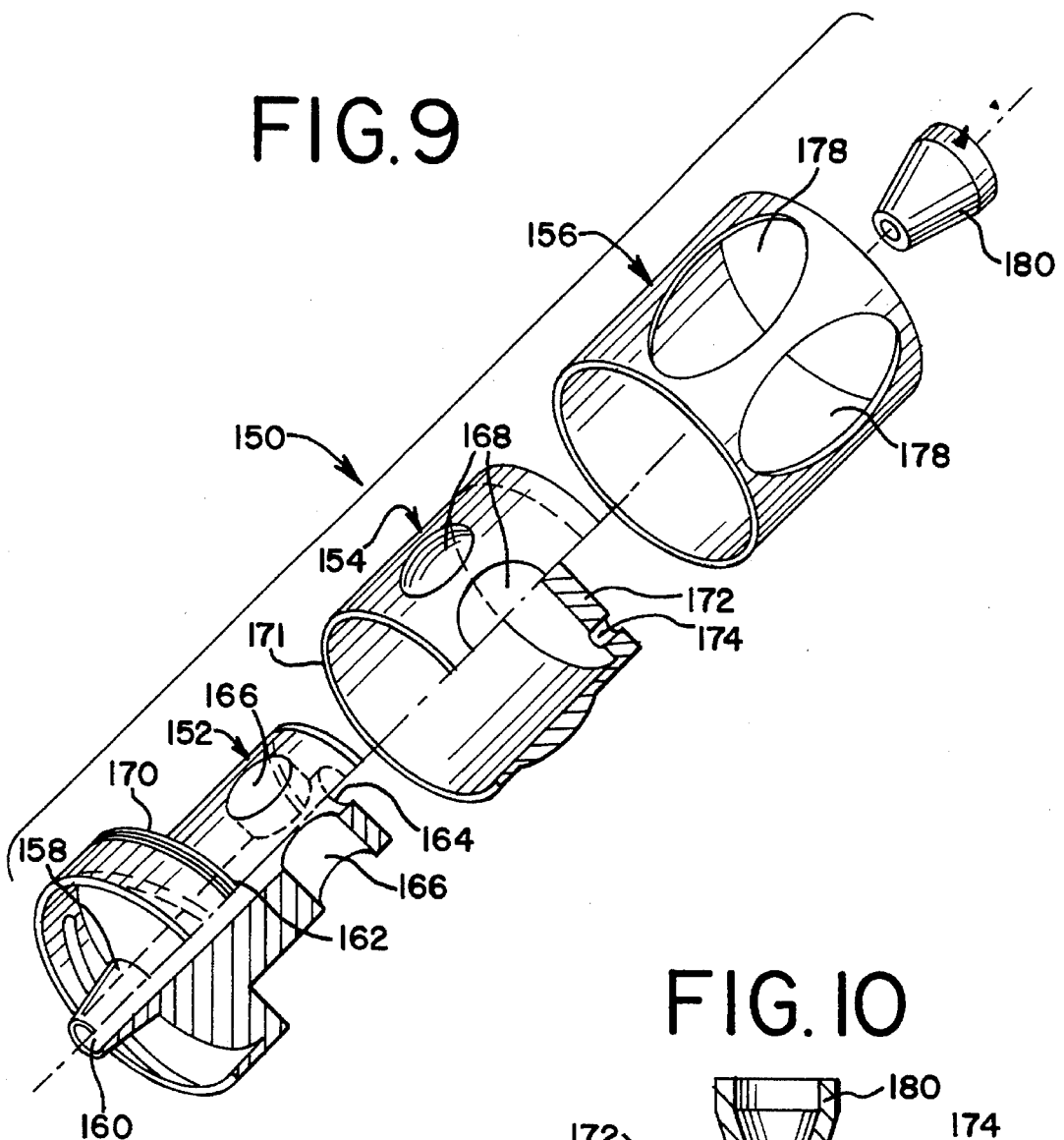
FIG. 9 is a perspective exploded view, with a cut away section, of another embodiment of the invention.
Figure 10:
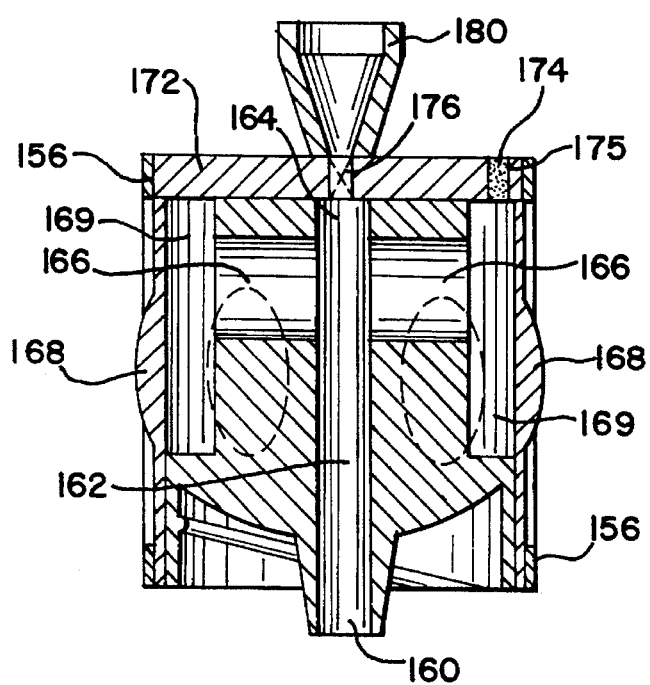
FIG. 10 is a cross-sectional view of the assembly of the embodiment of FIG. 9.

A fifth embodiment of the invention, which provides for tactile indication of vessel entry, is shown in FIGS. 9 and 10. Referring to FIG. 9, the device 150 includes a rigid inner member 152, a compliant intermediate member 154, and a rigid outer member 156. All three of the component members 152, 154, and 156 are preferably transparent to allow for visualization of blood passing within the device 150.

The rigid inner member 152 is generally cylindrical, and preferably includes a male luer lock fitting 158 having a distal opening 160. The luer lock fitting 158 permits the device to be connected to the proximal end of a standard vascular entry needle (not shown). A guideway 162 extends from the distal opening 160 of the male luer fitting to a proximal opening 164 of the rigid inner member 152. A pair of blood communication ports 166 form openings between the guideway 162 and the exterior of the rigid inner member 152.

The compliant intermediate member 154, shown partially cut away in FIG. 9 and in cross-sectional view in FIG. 10, has a circumferential wall 171 giving it a hollow cylindrical shape. Its distal end is open and its proximal end is closed by end wall 172. Compliant intermediate member 154 is made of a compliant elastomeric or flexible material, such as silicon rubber, urethane, Mylar, Nylon, PEBAX, or any other material that will form a compliant wall membrane which will move sufficiently in response to blood pressure within the device for tactile sensation. The amount of movement is a function of the material used, the wall thickness, and the area of the circumferential wall 171 against which the blood pressure acts.

The exterior surface of the circumferential wall 171 of the compliant intermediate member 154 preferably includes a plurality of tactile enhancing features, such as raised dimples 168 molded into the wall, as best seen in FIG. 9. Such features, also including, for example, ribs, bumps, dents, crenulations, and the like, facilitate tactile sensation of the compliant wall membrane as it moves, and may also enhance visual feedback of blood flow. The circumferential wall 171 may have variations in thickness or material type so that some areas are more compliant than others and will respond more dramatically to blood pressure changes. For example, the dimples 168 of the circumferential wall 171 could be formed with a thinner wall thickness than the surrounding wall in order to provide greater movement of the dimples under blood pressure.

The compliant intermediate member 154 fits over the narrower portion of the rigid inner member 152 and fits over a bonding rim 170 at the edge of the threaded luer lock fitting 158. A bonding cement, adhesive or mechanical connection may be used to attach and seal the compliant intermediate member 154 to the rigid inner member 152. The inner diameter of the compliant intermediate member 154 is larger than the outer diameter of the rigid inner member 152 so that a chamber 169 is defined between the two, as best seen in FIG. 10.

End wall 172, located at the proximal end of the complaint intermediate member 154, includes an off-center air vent aperture 174 and a centrally-located slit 176, shown schematically as an "X" in FIG. 10. A gas permeable (and liquid impermeable) filter element 175 is disposed within or covering the vent aperture 174 and allows passage of air, but prevents the passage of blood through the aperture. The slit 176 blocks passage of blood, but allows passage of an elongated medical instrument in a manner similar to the barrier described in earlier embodiments.

The rigid outer member 156 is made of a relatively rigid transparent plastic material and has a hollow cylindrical shape with both ends open. It fits over the compliant intermediate member 154, attaching to the rigid inner member 152 at the bonding rim 170 with bonding cement, adhesive or mechanical connection, to form an outer support housing and to help secure the compliant intermediate member 154 in place. A plurality of large oval openings 178 are located side-by-side around the circumference of the rigid outer member 156. These openings 178 are aligned with the dimples 168, although larger, and provide touch access by a user of the device to the exterior surface of the compliant intermediate member 154. The raised dimples 168 are sized to protrude out slightly beyond the rigid outer member 156.

It should also be pointed out, however, that an outer support member, such as rigid outer member 156, is optional. No rigid outer member is absolutely necessary if the intermediate compliant member 154 is sufficiently firm to maintain its desired shape without such support.

A cone-shaped guide fitting 180, best seen in FIG. 9, is located at the proximal end of the device 150. As best seen in FIG. 10, the guide fitting 180 is disposed on the proximal wall 172 of the compliant intermediate member 154, by either molding it integrally with, or bonding to, the proximal wall 172. The opening of the guide fitting 180 is aligned with the slit 176 so that an elongated medical instrument inserted into the guide fitting 180 will be directed through the slit 176 and into the proximal guideway opening 164 of the rigid inner member 152. The guide fitting 180 facilitates initial entry of a "J"-tipped guide wire. Further, the interior passage of the guide fitting 180 preferably has a luer-compatible taper to facilitate attachment to the male luer fitting of a syringe or the like for flushing of the device if desired.

The device of FIGS. 9 and 10 functions in many respects as the previously described embodiments. Blood enters via an attached needle through the distal opening 160 of the luer lock fitting 158. The blood then travels up through the guideway 162, where it can be seen because the components are transparent. This provides an immediate visual indication that the attached vascular entry needle tip has entered a blood vessel.

The blood then flows through the blood pressure communication ports 166 and, with the next few pulses of blood, fills the chamber 169 defined between the compliant intermediate member 154 and the rigid inner member 152, as best seen in FIG. 10. This provides a further visual indication that the needle tip remains within the blood vessel. As blood fills the device, air is displaced through the vent aperture 174 to the outside environment, but no blood escapes because of the gas permeable filter element 175.

The embodiment of FIGS. 9 and 10 differs from the previously described embodiments in that when the device becomes filled and blood is blocked by the gas permeable filter member 175 within the vent aperture 174, blood pressure causes the compliant intermediate member 150 to bulge and then pulsate with the individual's heartbeat. This provides a user of the device with an ongoing tactile confirmation that the attached needle tip remains properly situated within the selected blood vessel.

It will also be understood by those skilled in the art that the previously described embodiments of FIGS. 1–8 can be modified to include a tactile confirmation feature simply by incorporating a compliant membrane responsive to blood pressure on an exterior wall of the device. This could be done, for example, either by making the entire outer wall member of a compliant (elastomeric or flexible) material, or by incorporating a smaller compliant membrane over a port or opening in an exterior wall of the device which would be in fluid communication with the blood within the device.

Once the attached vascular entry needle is properly positioned, an elongated medical instrument, such as a catheter or guide wire, can be inserted through the device and into the patient's blood vessel, as described above in connection with the preceding embodiments of the invention.

In a variation of the embodiment shown in FIGS. 9 and 10, no vent aperture 174 is included to allow displaced air to escape. In this case, blood fills the device only to the extent that air within the device can be compressed by the blood pressure. Blood may still be seen, thereby providing an initial visual indication that the needle tip has entered a blood vessel, but it will not fill the device. An ongoing indication of proper needle placement is still provided by pulsation of the compliant intermediate member 154. One possible benefit of this variation, is that the compliant intermediate member may respond more quickly because blood pressure will develop within the device almost immediately.

A sixth embodiment of the invention is shown as the blood containment device 190 in FIGS. 11 and 12. This embodiment also provides a combination of visual and tactile indication of proper needle placement.

As best seen in FIG. 11, the device 190 includes a transparent rigid inner member 192 and a transparent compliant outer member 194 made of elastomeric or flexible material. The rigid inner member 192 has an elongated tubular overall shape, male luer lock fitting 196 at its distal end for connection to a standard vascular entry needle (not shown) and a radially extending (or recessed) flange 206 at its proximal end.

A guideway 200 extends through the center of the rigid inner member 192 from a distal opening 198 to a proximal opening 202. A segment 201 of the guideway 200 near the proximal opening 202 of the inner rigid member 192 is tapered into a gradual funnel-like or female luer taper shape, with the wider portion being at the proximal opening 202 of the rigid inner member 192.

One or more blood communication passages 204 extend radially outward between the guideway 200 and the exterior surface of the rigid inner member 192. The flange 206 extending radially outward near the proximal end of the rigid inner member 192 provides a platform upon which a ring-shaped gas permeable filter member 210 rests. The flange 206 includes a pair of air vent notches 208 located opposite each other on the flange, which provide air passageways, as will be described below.

The compliant outer member 194 has an generally cylindrical, somewhat elongated overall shape with a slightly enlarged distal end that is open and a proximal end having an opening 218 and an inwardly projecting cone-shaped structure 216, as described further below. The inside diameter of the compliant outer member 194 is sized to fit over the flange 208 and luer lock fitting 196 of the rigid inner member 192, as best seen in FIG. 12.

A ridge 212 is formed around the interior circumference of the compliant outer member 194 near its distal end, as best seen in FIG. 11. When the device is assembled, as best seen in FIG. 12, the ridge 212 fits into a groove 214 formed near the distal end of the rigid inner member 192, and thereby secures the two members together. Bonding material may also be used if necessary to further secure the compliant outer member 194 to the inner rigid 192. As seen in FIG. 12, a blood containment chamber 211 is defined between the interior of the compliant outer member 194 and the exterior of the rigid inner member 192.

At the proximal end of the compliant outer member 194, a cone-shaped guideway 216, referred to above, projects downwardly from the proximal opening 218 into the interior of the compliant outer member 194. The cone-shaped guideway 216 is sized and shaped, with a male luer taper, to sealingly fit within the tapered female luer segment 201 of guideway 200 of the rigid inner member 192. The cone-shaped guideway 216 of the compliant outer member 194 facilitates insertion of a "J"-shaped catheter guide wire into the device, as well as the male luer fitting of a syringe or the like.

At the tip of the cone-shaped guideway 216 is located a barrier 220 having a slit formed therein, as shown schematically by the "X" in FIG. 12. As discussed in connection with the previously described embodiments, the slit in barrier 220 allows passage of an elongated medical instrument, but prevents passage of blood through the barrier.

A pair of vent passages 222 are provided in the wall of the proximal end of the compliant outer member 194, as best seen in FIG. 12. When the device is assembled, the vent passages 222 in the compliant outer member 194 communicate through the ring-shaped gas permeable filter element 210, and through the vent notches 208 of the rigid inner member 192, to the blood containment chamber 211. This allows air to vent to the atmosphere through the filter ring 210.

A plurality of ribs 224 are formed around the exterior of the compliant outer member 194. The ribs 224 are believed to enhance the tactile sensation provided by the device 190. Other tactile sensation enhancing features can also be used, as noted in connection with the embodiment of FIGS. 9 and 10.

The blood containment device 190 operates in much the same way as the embodiment of FIGS. 9 and 10. The inner rigid member 192 and compliant outer member 194 are transparent so that when a needle connected to the device punctures a blood vessel, the blood can be seen immediately as it enters the guideway 200. The blood then travels through the passages 204 and fills the blood containment chamber 211 defined between the exterior of the inner rigid member 192 and the interior of the compliant outer member 194. Air which is displaced by the blood is vented through the vent notches 208 of the filter platform flange 206, through the gas permeable filter element 210, and finally out through the vent passages 222 at the proximal end of the compliant outer member 194.

Once blood fills the device, it is blocked by the gas permeable filter element 210. The blood pressure then causes the compliant outer member 194 to bulge and then pulsate due to the patient's heartbeat. This provides a user of the device both an immediate indication that the attached vascular entry needle has entered a blood vessel, and an ongoing confirmation that the needle tip remains situated within the blood vessel.

Also, as noted in connection with the embodiment of FIGS. 9 and 10, the air vent passages and hydrophobic filter are optional. The device will operate without venting displaced air and, in fact, will provide a tactile indication of blood pressure more quickly in such case. One disadvantage, however, may be that when a patient has very low blood pressure visual observation of blood slowly filling the device may be more practical than tactile confirmation.

It should also be noted that an outer rigid frame member could be used over the compliant outer member 194 in the blood containment device 190, if desired, provided it allows for a tactile blood pressure indication which is accessible to a user of the device. It will thus be recognized, as previously noted, that one skilled in the art could incorporate such a feature in a large variety of designs, all of which would be within the scope of the present invention.

From the foregoing, it can be seen that a blood containment device for use with a vascular entry needle has been provided which fully meets the objects of the instant invention. In each of the above-described embodiments, it is possible to determine-by visual and/or tactile indications-that an attached vascular entry needle has entered a blood vessel and remains properly positioned within the blood vessel. Moreover, the blood is safely contained within the device. An elongated medical instrument, such as a guide wire or catheter, can be inserted through the device and into a selected blood vessel.

The embodiments described above use from a one to three stage visualization channel. It will be recognized, however, that any combination of the different stages of the visualization channel could be used, and that a wide variety of shapes and sizes will be readily apparent to one skilled in the art. Moreover, it will also be recognized that the tactile confirmation feature of the invention can be used alone or in combination with any of the embodiments described above.

Accordingly, while the device has been described in terms of the above embodiments, there is no intent to limit the invention to the same. On the contrary, it is intended to cover all modifications and equivalents within the scope of the appended claims.

What is claimed is:

1. A blood containment device for use with a vascular entry needle, comprising:
    a main body portion including a distal opening and a proximal opening and a guideway extending therebetween, said distal opening being adapted to communicatively connect to a vascular entry needle, and said proximal opening being adapted to receive an elongated medical instrument for passage through said guideway and said vascular entry needle;
    a barrier disposed in said guideway between said proximal and distal openings which prevents passage of blood through said guideway but allows passage therethrough of an elongated medical instrument; and
    said main body portion including a touch accessible compliant member in fluid communication with said distal opening of the device such that blood pressure at said distal opening is transmitted to said compliant or flexible member, thereby causing said compliant member to move responsively to changes in blood pressure at said distal opening.

2. The blood containment device of claim 1, wherein said barrier disposed in said guideway comprises a penetrable elastomeric wall which includes a normally-closed preformed aperture that facilitates penetration thereof by an elongated medical instrument.

3. The blood containment device of claim 1, wherein said main body portion comprises an outer member having an exterior and an interior surface and an inner member having an exterior and an interior surface, said inner member fitting within said outer member to define a blood containment chamber therebetween, and said outer member including said compliant or flexible member.

4. The device of claim 3, wherein said blood containment chamber comprises a cylindrically shaped space defined around the interior surface of said outer member and the exterior surface of said inner member.

5. The blood containment device of claim 3, further including a gas permeable member disposed between the blood containment chamber and outside environment to allow the venting of air from said chamber.

6. The blood containment device of claim 1, further including a gas permeable member disposed between a blood containment chamber and outside environment to allow the venting of air from said chamber.

7. The blood containment device of claim 1, wherein said compliant or flexible member contains a tactile enhancing structure on the surface.

8. The device of claim 7, wherein said tactile enhancing structure includes one or more dimples.

9. The device of claim 7, wherein said tactile enhancing structure includes one or more ribs.

10. The blood containment device of claim 1, wherein said compliant or flexible member contains at least one area of reduced thickness which provides greater movement in response to changes in blood pressure within the device than areas of unreduced thickness.

11. The blood containment device of claim 1, wherein said compliant or flexible member is made of material selected from the group silicon rubber, urethane, Mylar, Nylon, and PEBAX.

12. The blood containment device of claim 1, wherein said main body portion comprises a rigid inner member with the guideway formed therethrough, a compliant or flexible intermediate member which fits around said rigid inner member, and a rigid outer member which fits around said compliant intermediate member but allows touch access to said compliant intermediate member.

13. The device of claim 12, wherein said compliant intermediate member includes tactile enhancing dimples which protrude out through openings in said rigid outer member.

14. The blood containment device of claim 1, wherein said guideway is tapered in a funnel-like shape at said proximal opening to facilitate the insertion of a "J"-tipped elongated medical instrument into the device.

15. A blood containment device for use with a vascular entry needle, providing both visual and tactile confirmation of proper needle placement, comprising:
    a main body portion including a distal opening and a proximal opening and a guideway extending therebetween, said distal opening being adapted to communicatively connect to a vascular entry needle, and said proximal opening being adapted to receive an elongated medical instrument for passage through said guideway and said vascular entry needle;
    a barrier disposed in said guideway between said proximal and distal openings which prevents passage of blood through said guideway but allows passage therethrough of an elongated medical instrument;
    a blood visualization channel communicating with said distal opening; and
    said main body portion including a touch accessible compliant member in fluid communication with said distal opening of the device such that blood pressure at said distal opening is transmitted to said compliant or flexible member, thereby causing said compliant member to move responsively to changes in blood pressure at said distal opening.

16. The blood containment device of claim 15, wherein said barrier disposed in said guideway comprises a penetrable elastomeric wall which includes a normally-closed pre-formed aperture that facilitates penetration thereof by an elongated medical instrument.

17. The blood containment device of claim 15, further including a gas permeable member disposed between a blood containment chamber and outside environment to allow the venting of air from said blood containment chamber.

18. The blood containment device of claim 15, wherein said main body portion comprises an outer member having an exterior and an interior surface and an inner member having an exterior and an interior surface, said inner member fitting within said outer member to define a blood containment chamber therebetween, and said outer member including said compliant or flexible member.

19. The blood containment device of claim 18, further including a gas permeable member disposed between the blood containment chamber and outside environment to allow the venting of air from said blood containment chamber.

20. The device of claim 19, wherein said blood containment chamber constitutes a portion of said blood visualization channel.

21. The device of claim 20, wherein said blood containment chamber comprises a cylindrically shaped space defined around the circumference of the interior surface of said outer member and the exterior surface of said inner member.

22. The blood containment device of claim 18, wherein said blood visualization channel and said blood containment chamber are coextensive.

23. The blood containment device of claim 15, wherein said compliant member contains one or more tactile enhancing structures on the surface.

24. The device of claim 23, wherein said tactile enhancing structures are dimples.

25. The device of claim 23, wherein said tactile enhancing structures are ribs.

26. The blood containment device of claim 15, wherein said compliant member contains at least one area of reduced thickness which provides greater movement in response to changes in blood pressure within the device than areas of unreduced thickness.

27. The blood containment device of claim 15, wherein said main body portion comprises a rigid inner member with the guideway formed therethrough, a compliant or flexible intermediate member which fits around said rigid inner member, and a rigid outer member which fits around said compliant intermediate member but allows touch access to said compliant intermediate member.

28. The device of claim 27, wherein said compliant or flexible intermediate member includes tactile enhancing dimples which protrude out through openings in said rigid outer member.

29. The blood containment device of claim 15, wherein said guideway is tapered in a funnel-like shape at said proximal opening to facilitate the insertion of a "J"-tipped elongated medical instrument into the device.

* * * * *

UNITED STATES PATENT AND TRADEMARK OFFICE
CERTIFICATE OF CORRECTION

PATENT NO. : 5,501,671

DATED : March 26, 1996

INVENTOR(S) : Jonathan J. Rosen; Richard A. Hillstead; Thomas D. Weldon; Charles E. Larsen; David O. Williams It is certified that error appears in the above-identified patent and that said Letters Patent is hereby corrected as shown below:

On the title page, References Cited, please add the following to U.S. Patent Documents:

--5,295,970 3/1994 Clinton et al. 604/168--

--5,295,969 3/1994 Fischell et al. 604/168--

Signed and Sealed this

Thirteenth Day of October 1998

Attest:

Attesting Officer

BRUCE LEHMAN

Commissioner of Patents and Trademarks